United States Patent [19]

Titzenthaler et al.

[11] 4,272,443

[45] Jun. 9, 1981

[54] SILVER-CONTAINING CARRIER CATALYSTS, PROCESS FOR THEIR MANUFACTURE, AND PROCESS FOR THE MANUFACTURE OF ETHYLENE OXIDE USING THESE CATALYSTS

[75] Inventors: Eckart Titzenthaler, Ludwigshafen; Roland Schwen, Friedelsheim, both of Fed. Rep. of Germany

[73] Assignee: BASF Aktiengesellschaft, Ludwigshafen, Fed. Rep. of Germany

[21] Appl. No.: 78,305

[22] Filed: Sep. 24, 1979

[30] Foreign Application Priority Data

Dec. 12, 1978 [DE] Fed. Rep. of Germany ....... 2844402

[51] Int. Cl.³ .................... C07D 301/10; B01J 21/08; B01J 23/04; B01J 23/50
[52] U.S. Cl. .............................. 260/348.34; 252/454
[58] Field of Search .................. 252/454; 260/348.34

[56] References Cited

U.S. PATENT DOCUMENTS

| | | | |
|---|---|---|---|
| 2,219,575 | 10/1940 | McNamee et al. | 252/454 X |
| 2,615,900 | 10/1952 | Sears | 252/476 X |
| 2,765,283 | 10/1956 | Sacken | 252/476 X |
| 3,585,217 | 6/1971 | Titzenthaler | 252/454 X |

*Primary Examiner*—W. J. Shine
*Attorney, Agent, or Firm*—H. Lawrence Jones

[57] ABSTRACT

This invention concerns a new carrier catalyst, the active mass of which contains silver, a process for its manufacture and a process for the manufacture of ethylene oxide by reacting oxygen-containing gases with ethylene by using this catalyst. This carrier catalyst comprising a carrier material and a catalyst, the active mass of which is 20 to 90 percent by weight of silver, 0.005 to 5 percent by weight of lithium, and 3 to 70 percent by weight of $SiO_2$ in free form or in the form of silicates, is extremely well suited for the manufacture of ethylene oxide by adding oxygen to ethylene.

4 Claims, No Drawings

SILVER-CONTAINING CARRIER CATALYSTS, PROCESS FOR THEIR MANUFACTURE, AND PROCESS FOR THE MANUFACTURE OF ETHYLENE OXIDE USING THESE CATALYSTS

BACKGROUND OF THE INVENTION

1. Field of the Invention

This invention relates to catalysts containing silver for use in the preparation of ethylene oxide.

2. Description of the Prior Art

In German Patent Application No. 1,279,007, there are disclosed catalysts, the active mass of which consists primarily of silver silicate. These catalysts are extremely well suited for the manufacture of ethylene oxide by adding oxygen to ethylene, where they are used as catalysts according to the techniques of the fluidized bed process. To date, however, technically applicable carrier catalysts for fixed bed reactions using silver silicate could not be produced since the silver silicate does not adhere sufficiently to the carrier materials and since such catalysts, therefore, have an extremely short service life. Thus, this invention resulted from the recognized need to produce carrier catalysts with increased service life, the active mass of which contained silver silicate or silver compounds and silicates.

SUMMARY OF THE INVENTION

It has been found that carrier catalysts with high service life containing silver in the active mass, can be obtained if carrier materials are coated with a suspension containing 0.001 to 2 percent solids by weight of lithium in the form of a water-soluble Li-silicate compound and 5 to 50 percent by weight of silver in the form of a water-insoluble halogen-free silver compound. After coating, the carrier materials are dried to produce the carrier catalysts.

These carrier catalysts comprise a carrier material and a catalyst, the active mass of which is 20 to 90 percent by weight, preferably 40 to 90 percent by weight, of silver, 0.005 to 5 percent by weight, preferably 0.5 to 1.5 percent by weight, of lithium, and 3 to 70 percent by weight, preferably 4 to 55 percent by weight, of $SiO_2$ in free form or in the form of silicates, are extremely well suited for the manufacture of ethylene oxide by adding oxygen to ethylene. For this purpose, a mixture of 6 to 30 volume percent of ethylene, 5 to 20 volume percent of oxygen, and the remainder of inert gases such as nitrogen, is directed over a fixed bed of these carrier catalysts in the well-known manner at temperatures of 180° to 280° C. under a pressure of 1 to 30 bar.

DETAILED DESCRIPTION OF THE INVENTION

The aqueous solutions of Li-silicate compounds required for the manufacture of the catalysts are either commercially available lithium-water glass or those types which may be produced therefrom by adding water or $SiO_2$. All of these types are not solutions of defined lithium silicates but mixtures of various lithium silicates and polysilicic acids. The calculatory-molar ratio of $Li_2O$ to $SiO_2$ is therefore generally stated to characterize these solutions. In the case of the solutions to be used according to this invention, this ratio is preferably between 1:3 and 1:13.

Silver oxide, silver silicate, and silver carbonate are especially well suited as water-insoluble silver compounds but, in addition to these, organic salts such as silver oxylate, and silver lactate, are also suited for this purpose. Halogen-containing silver compounds are not suitable since it is known that halogen inhibits ethoxylation. The preferred amount of silver compounds is 10 to 50 percent by weight of silver relative to the amount of the coating suspension.

The components in the suspensions—lithium-water glass and silver compounds—form a solid mass at room temperature after some time so that it is recommended to coat the carrier materials immediately following the mixing of these components. The mixture can be applied to the carrier materials according to well-known techniques. Preferably, according to the coating process of the invention only one coating pass is required. However, multiple coating can be used for those carrier materials which, like glass, have a very smooth surface. Drying generally takes place at 20° to 100° C. and requires approximately 2 to 24 hours. The resulting catalysts contain approximately 2 to 60 percent by weight of active mass. Preferred are those catalysts which contain 5 to 12 percent by weight of active mass. Exemplary carrier materials are the commonly used carrier materials including primarily those which are commercially available such as silicic acid or alpha-aluminum oxide in the form of spheres, tablets or sections. The dimensions of these particles are appropriately 5 to 8 millimeters in diameter and, in the case of tablets and sections, up to 8 millimeters in length. In addition to the above-referenced components, the active mass of the carrier catalysts according to this invention may contain other materials such as activators, for instance, containing 0.001 to 0.02 percent by weight of sodium, 0.001 to 0.2 percent by weight of caesium, 0.01 to 2 percent by weight of calcium, and 0.01 to 0.5 percent by weight of aluminum, namely, in the form of their oxides, hydroxides, nitrates, carbonates, or other halogen-free salts.

The required amount of catalyst depends primarily upon its silver content. At 220° C. and under normal pressure, approximately 0.2 to 0.5 kilograms of ethylene oxide are normally obtained per hour, per kilogram silver. The conversion to ethylene oxide which is commonly relative to the oxygen is generally 35 to 45 percent and the yield relative to this is approximately 70 to 75 percent. Otherwise, the same conditions commonly used for fixed bed processes using traditional carrier catalysts are applied for the manufacture of the ethylene oxide. Thus, the reaction is brought about at 180° to 280° C., preferably between 200° and 250° C., and a pressure of 1 to 30, preferably 1 to 20, bars. 6 to 30 volume percent of the applied gas mixture consists of ethylene, 5 to 20 volume percent of oxygen and the remainder consists of inert gases such as nitrogen, carbon dioxide, and methane. Instead of said inert gas component, other gaseous materials may also be used which promote the reaction such as water, as well as slight quantities of ethylene dichloride, in order to suppress secondary reactions. Under the conditions of ethoxylation, the silver, which is initially present in its ionic form, is reduced to metal.

The gas mixture obtained after the reaction is treated as usual, for instance, by washing the ethylene oxide with water and by isolating it by means of distillation from the resulting solutions. The other gases can be recycled. The catalysts according to this invention can be produced easily and according to sound environmental methods, they supply good ethoxylation results and are characterized by a long service life.

The following examples illustrate the various aspects of the invention. Where not otherwise specified throughout this specification and claims, temperatures are in degrees centigrade, and parts, percentages and proportions are by weight.

EXAMPLE 1

Porous alpha-aluminum oxide spheres having a diameter of 5 millimeters, in the amount of 200 grams, were coated with a freshly prepared suspension consisting of 16 grams silver silicate, 16 grams lithium-water glass, and 16 grams of twice-distilled water in a coating drum. The suspension contained 16.7 percent by weight of silver, 0.14 percent by weight of lithium, and 23.3 percent by weight of $SiO_2$ and in addition, as impurities in the silver silicate, 0.096 percent by weight of potassium, 0.063 percent by weight of barium and 0.013 percent by weight of aluminum.

The lithium-water glass used consisted of 9.6 grams of a commercially available product (solids content about 22 percent by weight, ratio of $Li_2O:SiO_2$ equal to 1:4.8) and 6.4 grams of pure $SiO_2$ solution having a $SiO_2$ content of 20 percent by weight (remainder water). The ratio of $Li_2O:LiO_2$ in this mixture was 1:8.0. The silver silicate was precipitated according to known methods at 100° C. with potassium-water glass from approximately a 10 percent by weight aqueous silver nitrate solution. It was washed until it was largely free of alkali and nitrates, then dried, and ground to a particle size of 0.1 millimeters.

The coated spheres were then dried at room temperature for 24 hours and until a constant weight was reached at 100° C. in a vacuum drying chamber (roughly 24 hours). The active mass of the completed catalyst contained 41.3 percent by weight of silver, 0.5 percent by weight of lithium, and 58 percent by weight of $SiO_2$ and further, in quantities below 0.3 percent by weight, the trace elements K, Ba and Al.

The catalyst, in the amount of 200 grams, was placed in a glass pipe having an internal diameter of 22 millimeters as a fixed bed. The pipe was subsequently charged at an hourly flow rate with a gas mixture at 240°C. and a pressure of 1 bar consisting of 5 liters ethylene, 1 liter oxygen, 7 liters carbon dioxide, 82 liters nitrogen, and 3 milliliters ethylene dichloride. The oxygen conversion was 41 percent and the ethylene oxide yield, relative to the oxygen, was 75 percent.

EXAMPLE 2

With a catalyst consisting of 200 grams of the aluminum oxide spheres as carrier material and 23 grams of active mass containing 35 percent by weight silver, 1.4 percent by weight of lithium, 63 percent by weight of $SiO_2$ and 0.2 percent by weight of potassium, produced according to the procedure of Example 1, the ethoxylation conditions set forth in Example 1 were repeated except that 40 milliliters of ethylene chloride were used. An oxygen conversion of 41 percent was obtained and an ethylene oxide yield relative to the oxygen conversion of 71 percent was achieved.

EXAMPLE 3

Glass spheres in the amount of 1250 grams, having a diameter of 5 millimeters, were coated with a freshly prepared suspension consisting of 20 grams silver silicate and 40 grams of a commercially available lithium water glass (lithium content 1 percent by weight, $Li_2O:SiO_2=1:4.8$) in a coating drum and the mixture was subsequently dried for 24 hours. This process was repeated three times so that a total of 80 grams of silver silicate and 160 grams of lithium-water glass were applied to the glass spheres.

The active mass of the completed catalyst contained 35 percent by weight of silver, 1.4 percent by weight of lithium and 63 percent by weight of $SiO_2$ and in addition, in quantities of less than 0.3 percent by weight, the trace elements potassium, barium and aluminum.

At 220° C. and 1 bar of pressure, a gas mixture consisting of 29 liters ethylene, 50 liters methane, 8 liters oxygen, 7 liters carbon dioxide, 3 liters argon, 3 liters nitrogen and 20 milliliters ethylene dichloride was directed over 250 grams of this catalyst per hour. The oxygen conversion was 50 percent and the ethylene oxide yield related to the oxygen was 71 percent.

EXAMPLE 4

Spheres made of sintered corundum in the amount of 200 grams, having a diameter of 5 millimeters, were coated with a freshly prepared suspension consisting of 30 grams silver silicate, 30 grams of commercially available potassium-containing lithium-water glass (lithium content 1 percent by weight) and 15 grams of double-distilled water, in a coating drum and were subsequently dried. The active mass of the completed catalyst contained 34 percent by weight of silver, 0.85 percent by weight of lithium, 0.02 percent by weight of potassium, and 65 percent by weight of $SiO_2$. Under the ethoxylation conditions of Example 1, but with 20 milliliters of ethylene dichloride, an oxygen conversion of 41 percent and an ethylene oxide yield of 72 percent, relative to the oxygen, was achieved with this catalyst.

EXAMPLE 5

Spheres made of sintered corundum in the amount of 200 grams, having a diameter of 5 millimeters, were coated with a freshly prepared suspension consisting of 15 grams silver silicate, 5 grams silver-iodide-oxide, 15 grams of lithium-water glass (lithium content 1 percent by weight) and 15 grams of double-distilled water and were subsequently dried. The active mass of the completed catalyst contained 53 percent by weight silver, 0.7 percent by weight of lithium, and 46 percent by weight of $SiO_2$ as well as the accompanying trace elements potassium, barium, and aluminum in quantities below 0.2 percent by weight. Under the ethoxylation conditions set forth in Example 1, but with 6 milliliters of ethylene dichloride, use of this catalyst resulted in an oxygen conversion of 36 percent and an ethylene oxide yield related to the oxygen conversion of 74 percent.

EXAMPLE 6

Spheres made of sintered corundum in the amount of 40 kilograms, having a diameter of 5 millimeters, were coated in a coating drum with a freshly prepared suspension consisting of 4 kilograms silver-iodide-oxide, 1 kilogram lithium-water glass (lithium content 1 percent by weight), 7 kilograms of double-distilled water, and 9.5 grams of caesium (in the form of CsOH). The silver-iodide-oxide was freshly precipitated from silver nitrate with LiOH at 100° C. and was washed nitrate and alkali-free several times with double-distilled water. From its manufacture, it retained 2 kilograms of water which were already included in the above-referenced quantity of 7 kilograms. The active mass of the completed catalysts contained 88 percent by weight of silver, 0.24 percent by weight of lithium, 4.7 percent by weight of SiO$_2$ and 0.23 percent by weight of caesium.

Under the ethoxylation conditions of Example 3, but without ethylene dichloride, an average oxygen conversion of 37 percent and an ethylene oxide yield of 70 percent, relative to the oxide yield, was achieved with this catalyst in a semi-industrial scale pilot plant over an operation period of 3 weeks.

While this invention has been described with reference to certain specific embodiments, it will be recognized by those skilled in the art that many variations are possible without departing from the spirit and scope of the invention.

What is claimed is:

1. A carrier catalyst comprising a carrier material and a catalyst, the active mass of which is 20 to 90 percent by weight of silver, 0.005 to 5 percent by weight of lithium; and 3 to 70 percent by weight of SiO$_2$ in free form or in the form of silicates.

2. The carrier catalyst of claim 1, the active mass of which comprises 40 to 90 percent by weight of silver, 0.5 to 1.5 percent by weight of lithium, and 4 to 55 percent by weight of SiO$_2$.

3. A process for the manufacture of the carrier catalyst according to claims 1 or 2 comprising (1) coating said carrier materials with an aqueous suspension containing 0.001 to 2 percent by weight of lithium, in the form of a water-soluble Li-silicate compound, and 5 to 50 percent by weight of silver, in the form of a water-insoluble halogen-free silver compound, and (2) drying the coated carrier materials.

4. In the process for the manufacture of ethylene oxide by adding oxygen to ethylene in which a mixture of 6 to 30 volume percent of ethylene, 5 to 20 volume percent of oxygen and the remainder of inert gases such as nitrogen are passed over a fixed catalyst bed at 180°–280° C. and under a pressure of 1 to 30 bar, the improvement wherein the process is conducted in the presence of the carrier catalysts of claims 1 or 2.

* * * * *